US011834665B2

(12) United States Patent
Smanski et al.

(10) Patent No.: US 11,834,665 B2
(45) Date of Patent: Dec. 5, 2023

(54) PROGRAMMABLE TRANSCRIPTION FACTORS AND METHODS

(71) Applicant: REGENTS OF THE UNIVERSITY OF MINNESOTA, Minneapolis, MN (US)

(72) Inventors: Michael J. Smanski, Minneapolis, MN (US); Maciej Maselko, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 770 days.

(21) Appl. No.: 16/611,008

(22) PCT Filed: May 10, 2018

(86) PCT No.: PCT/US2018/031950
§ 371 (c)(1),
(2) Date: Nov. 5, 2019

(87) PCT Pub. No.: WO2018/209014
PCT Pub. Date: Nov. 15, 2018

(65) Prior Publication Data
US 2020/0157552 A1  May 21, 2020

Related U.S. Application Data

(60) Provisional application No. 62/504,260, filed on May 10, 2017.

(51) Int. Cl.
*C12N 15/63* (2006.01)
*C12N 9/22* (2006.01)
*C12N 15/11* (2006.01)

(52) U.S. Cl.
CPC .............. *C12N 15/635* (2013.01); *C12N 9/22* (2013.01); *C12N 15/11* (2013.01); *C12N 2310/20* (2017.05); *C12N 2800/80* (2013.01); *C12N 2830/002* (2013.01); *C12N 2830/005* (2013.01)

(58) Field of Classification Search
CPC .................................................. C12N 15/635
See application file for complete search history.

(56) References Cited

U.S. PATENT DOCUMENTS

| | | |
|---|---|---|
| 9,125,388 B2 | 9/2015 | Alphey et al. |
| 10,376,925 B2 | 8/2019 | Mingyan |
| 2004/0082032 A1 | 4/2004 | Bovi et al. |
| 2006/0147978 A1 | 7/2006 | Lorens et al. |
| 2009/0155854 A1 | 6/2009 | Yueh et al. |
| 2013/0298266 A1 | 11/2013 | Alphey et al. |
| 2014/0356958 A1 | 12/2014 | Mali et al. |
| 2015/0064138 A1 | 3/2015 | Lu et al. |
| 2017/0204407 A1* | 7/2017 | Gilbert ............... C12N 15/1082 |
| 2018/0327762 A1 | 11/2018 | Maselko et al. |
| 2020/0140885 A1 | 5/2020 | Hay et al. |
| 2020/0157552 A1 | 5/2020 | Smanski et al. |
| 2022/0015339 A1 | 1/2022 | Maselko et al. |

FOREIGN PATENT DOCUMENTS

| | | |
|---|---|---|
| WO | WO 2006/060603 A2 | 6/2006 |
| WO | WO 2014/096428 A1 | 6/2014 |
| WO | WO 2015/084802 A1 | 6/2015 |
| WO | WO 2017/083501 A1 | 5/2017 |
| WO | WO 2018/209014 A1 | 11/2018 |
| WO | WO 2020/101947 A2 | 6/2020 |
| WO | WO 2021/076342 A2 | 4/2021 |
| WO | WO 2021/087319 A1 | 5/2021 |

OTHER PUBLICATIONS

Piatek, Agnieszka, and Magdy M. Mahfouz. "Targeted genome regulation via synthetic programmable transcriptional regulators." Critical reviews in biotechnology 37.4 (2017): 429-440. (Year: 2017).*
Dijken, Anja JH van, Henriette Schluepmann, and Sjef CM Smeekens. "*Arabidopsis* trehalose-6-phosphate synthase 1 is essential for normal vegetative growth and transition to flowering." Plant physiology 135.2 (2004): 969-977. (Year: 2004).*
Jusiak, Barbara, et al. "Engineering synthetic gene circuits in living cells with CRISPR technology." Trends in biotechnology 34.7 (2016): 535-547 (Year: 2016).*
Shalem, Ophir, Neville E. Sanjana, and Feng Zhang. "High-throughput functional genomics using CRISPR-Cas9." Nature Reviews Genetics 16.5 (2015): 299-311. (Year: 2015).*
Liu, Y. et al. (2014) Synthesizing AND gate genetic circuits based on CRISPR-Cas9 for identification of bladder cancer cells. Nat. Commun. 5, 5393 (Year: 2014).*
Kumar, Dhinesh, et al. "GAL4 transactivation-based assay for the detection of selective intercellular protein movement." Plasmodesmata: Methods and Protocols (2015): 231-243 (Year: 2015).*
International Patent Application No. PCT/US2016/061297, filed Nov. 10, 2016; International Preliminary Report on Patentability dated May 24, 2018; 11 pages.
International Patent Application No. PCT/US2016/061297, filed Nov. 10, 2016; International Search Report / Written Opinion dated Mar. 2, 2017; 18 pages.

(Continued)

*Primary Examiner* — Weihua Fan
(74) *Attorney, Agent, or Firm* — Mueting Raasch Group (57) ABSTRACT

This disclosure describes a programmable transcription factor system. Generally, the system includes a programmable transcription factor, a polynucleotide that includes a coding region whose expression is either required or toxic for cell viability, and a promoter operably linked to the polynucleotide and having a binding site for the programmable transcription factor. The programmable transcription factor generally includes a domain that specifically binds to a promoter and a domain that either activates transcription (if the polynucleotide encodes an essential product) or represses transcription (if the polynucleotide encodes a toxic product).

12 Claims, 2 Drawing Sheets
Specification includes a Sequence Listing.

(56) References Cited

OTHER PUBLICATIONS

International Patent Application No. PCT/US2018/031950, filed May 10, 2018; International Preliminary Report on Patentability dated Nov. 12, 2019; 7 pages.
International Patent Application No. PCT/US2018/031950, filed May 10, 2018; International Search Report / Written Opinion dated Jul. 23, 2018; 11 pages.
International Patent Application No. PCT/US2019/059826, filed Nov. 5, 2019; International Preliminary Report on Patentability dated May 11, 2021; 6 pages.
International Patent Application No. PCT/US2019/059826, filed Nov. 5, 2019; International Search Report / Written Opinion dated May 21, 2020; 9 pages.
International Patent Application No. PCT/US2020/053749, filed Oct. 1, 2020; International Preliminary Report on Patentability dated Apr. 14, 2022, 10 pages.
International Patent Application No. PCT/US2020/053749, filed Oct. 1, 2020; International Search Report / Written Opinion dated Jul. 23, 2021; 14 pages.
International Patent Application No. PCT/US2020/058301, filed Oct. 30, 2020; International Search Report / Written Opinion dated Feb. 22, 2021; 10 pages.
International Patent Application No. PCT/US2020/058301, filed Oct. 31, 2019; International Preliminary Report on Patentability dated Feb. 22, 2021; 9 pages.
Akbari et al., Biosafety. Safeguarding gene drive experiments in the laboratory. Science 349, 927-929 (2015).
Aliota et al., The wMel strain of Wolbachia Reduces Transmission of Zika virus by Aedes aegypti. Sci Rep 6, 28792 (2016).
Alphey et al., Genetic control of Aedes mosquitoes. Pathog Glob Health 107, 170-179 (2013).
Alphey et al., Malaria control with genetically manipulated insect vectors. Science 298, 119-121 (2002).
Alphey et al., Sterile-insect methods for control of mosquito-borne diseases: an analysis. Vector Borne Zoonotic Dis 10, 295-311 (2010).
Alphey, Genetic control of mosquitoes. Annu Rev Entomol 59, 205-224 (2014).
Annaluru et al., Total synthesis of a functional designer eukaryotic chromosome. Science 344, 55-58 (2014).
Bai, "Homology-integrated CRISPR-Cas (HI-CRISPR) system for one-step multigene disruption in *Saccharomyces cerevisiae*" 2014 ACS Synth Biol 4(5):585-594.
Bain, et al., Non-GMO vs organic labels: purity or process guarantees in a GMO 260 contaminated landscape. Agric. Human Values 34, 805-818 (2017).
Bajer et al. Partial migration to seasonally-unstable habitat facilitates biological invasions in a predator-dominated system. Oikos, 124: 1520-1526 (2015).
Bank et al., The limits to parapatric speciation: Dobzhansky-Muller incompatibilities in a continent-island model. Genetics 191, 845-863 (2012).
Baryshnikova et al., Quantitative analysis of fitness and genetic interactions in yeast on a genome scale. Nat Methods 7, 1017-1024 (2010).
Beckmann et al., A Wolbachia deubiquitylating enzyme induces cytoplasmic incompatibility. Nat Microbiol 2, 17007 (2017).
Bikard et al., Programmable repression and activation of bacterial gene expression using an engineered CRISPR-Cas system. Nucleic Acids Res 41, 7429-7437 (2013).
Black et al., Why RIDL is not SIT. Trends Parasitol 27, 362-370 (2011).
Boeke et al., Genome Engineering. The Genome Project—Write. Science 353, 126-127 (2016).
Boete et al., Impact of mating behaviour on the success of malaria control through a single inundative release of transgenic mosquitoes. J Theor Biol 347, 33-43 (2014).
Breyer et al., Biosafety considerations associated with molecular farming in genetically modified plants Journal of Medicinal Plants Research (2009), 3(11): 825-838.
Buchman et al., Site-specific transgenesis of the *Drosophila melanogaster* Y-chromosome using CRISPR/Cas9. Insect Mol Biol 28, 65-73 (2019).
Bull et al., The gene drive bubble: New realities. PLoS Genet 13, e1006850 (2017).
Burgos et al., The impact of herbicide-resistant rice technology on phenotypic diversity and population structure of United States weedy rice. Plant Physiol 166, 1208-1220 (2014).
Caceres, Mass rearing of temperature sensitive genetic sexing strains in the Mediterranean fruit fly (*Ceratitis capitata*). Genetica 116, 107-116 (2002).
Carvalho et al., Mass production of genetically modified Aedes aegypti for field releases in Brazil. J Vis Exp, e3579 (2014).
Champer et al., Cheating evolution: engineering gene drives to manipulate the fate of wild populations. Nat Rev Genet 17, 146-159 (2016).
Champer et al., Novel CRISPR/Cas9 gene drive constructs reveal insights into mechanisms of resistance allele formation and drive efficiency in genetically diverse populations. PLoS Genet 13, e1006796 (2017).
Chappell et al., A renaissance in RNA synthetic biology: new mechanisms, applications and tools for the future. Curr Opin Chem Biol 28, 47-56 (2015).
Chavez et al., Comparison of Cas9 activators in multiple species. Nat Methods 13, 563-567 (2016).
Chen et al., Naturally occurring incompatibilities between different Culex pipiens pallens populations as the basis of potential mosquito control measures. PLoS Negl Trop Dis 7, e2030 (2013).
Cherry et al., *Saccharomyces* Genome Database: the genomics resource of budding yeast. Nucleic Acids Res 40, D700-705 (2012).
Concha et al., A transgenic male-only strain of the New World screwworm for an improved control program using the sterile insect technique. BMC Biol 14, 72 (2016).
Condon et al. Genetic sexing through the use of Y-linked transgenes. Insect Biochem Mol Biol. Nov. 2007;37(11):1168-76.
Davis et al., Engineered underdominance allows efficient and economical introgression of traits into pest populations. J Theor Biol 212, 83-98 (2001).
Deliberto et al., "Hybrid Rice Production Costs and Returns : Comparisons with conventional clearfield varieties," 2010, LSU AgCenter Staff Rep., 1-8.
Dicarlo et al., Genome engineering in *Saccharomyces cerevisiae* using CRISPR-Cas systems. Nucleic Acids Res 41, 4336-4343 (2013).
Dobzhansky et al. Studies on hybrid sterility—I. Spermatogenesis in pure and hybrid *Drosophila pseudoobscura*. Zeitschrift für Zellforsch. und Mikroskopische Anat. 21, 169-223 (1934).
Dobzhansky, Studies on Hybrid Sterility. II. Localization of Sterility Factors in Drosophila Pseudoobscura Hybrids. Genetics 21, 113-135 (1936).
Dodson et al., Wolbachia enhances West Nile virus (WNV) infection in the mosquito *Culex tarsalis*. PLoS Negl Trop Dis 8, e2965 (2014).
Dominiak et al., Evaluating irradiation dose for sterility induction and quality control of mass-produced fruit fly *Bactrocera tryoni* (Diptera: Tephritidae). J Econ Entomol 107, 1172-1178 (2014).
Dong et al. Synthetic CRISPR-Cas gene activators for transcriptional reprogramming in bacteria. Nat Commun 9, 2489 (2018).
Drubin et al., Yeast actin-binding proteins: evidence for a role in morphogenesis. J Cell Biol 107, 2551-2561 (1988).
Dyck, et al., A. S. Sterile insect technique: principles and practice in area-wide integrated pest management (Springer 2005).
Dye, Models for the Population Dynamics of the Yellow Fever Mosquito, Aedes Aegypti, Journal of Animal Ecology 53(1):247-268 (1984).
Engler et al., A golden gate modular cloning toolbox for plants. ACS Synth Biol 3, 839-843 (2014).
Esvelt et al., Concerning RNA-guided gene drives for the alteration of wild populations. Elife 3, (2014).

(56) References Cited

OTHER PUBLICATIONS

Esvelt et al., Orthogonal Cas9 proteins for RNA-guided gene regulation and editing. Nat Methods 10, 1116-1121 (2013).
Evdokimov et al., Structural basis for the fast maturation of Arthropoda green fluorescent protein. EMBO Rep 7, 1006-1012 (2006).
Ewen-Campen et al., Optimized strategy for in vivo Cas9-activation in Drosophila. Proc Natl Acad Sci U S A 114, 9409-9414 (2017).
Facchinelli et al., Field cage studies and progressive evaluation of genetically-engineered mosquitoes. PLoS Negl Trop Dis 7, e2001 (2013).
Fernando et al., Molecular circuits for associative learning in single-celled organisms. J R Soc Interface 6, 463-469 (2009).
Fu et al., Female-specific flightless phenotype for mosquito control. Proc Natl Acad Sci U S A 107, 4550-4554 (2010).
Galizi et al., A synthetic sex ratio distortion system for the control of the human malaria mosquito. Nat Commun 5, 3977 (2014).
Gallagher et al., Multilayered genetic safeguards limit growth of microorganisms to defined environments. Nucleic Acids Res 43, 1945-1954 (2015).
Gallwitz et al., Molecular cloning of the actin gene from yeast Saccharomyces cerevisiae. Nucleic Acids Res 8, 1043-1059 (1980).
Gantz et al., Genome editing. The mutagenic chain reaction: a method for converting heterozygous to homozygous mutations. Science 348, 442-444 (2015).
Gantz et al., Highly efficient Cas9-mediated gene drive for population modification of the malaria vector mosquito Anopheles stephensi. Proc Natl Acad Sci U S A 112, E6736-6743 (2015).
Gao et al., Comparison of TALE designer transcription factors and the CRISPR/dCas9 in regulation of gene expression by targeting enhancers. Nucleic Acids Res 42, e155 (2014).
Geng et al., Saccharomyces cerevisiae Rab-GDI displacement factor ortholog Yip3p forms distinct complexes with the Ypt1 Rab GTPase and the reticulon Rtn1p. Eukaryot Cell 4, 1166-1174 (2005).
Gietz et al., Yeast transformation by the LiAc/SS Carrier DNA/PEG method. Methods Mol Biol 313, 107-120 (2006).
Goindin et al., Parity and longevity of Aedes aegypti according to temperatures in controlled conditions and consequences on dengue transmission risks. PLoS One 10, e0135489 (2015).
Gressel, "Dealing with transgene flow of crop protection traits from crops to their relatives" May 2014 Pest Mgmt. Sci., 10 pgs. DOI 10.01008/ps.8350.
Grether et al., The head involution defective gene of Drosophila melanogaster functions in programmed cell death. Genes Dev 9, 1694-1708 (1995).
Guillier et al., Automated image analysis of bacterial colony growth as a tool to study individual lag time distributions of immobilized cells. J Microbiol Methods 65, 324-334 (2006).
Gutierrez et al., A model describing the effect of sex-reversed YY fish in an established wild population: The use of a Trojan Y chromosome to cause extinction of an introduced exotic species. J Theor Biol 241, 333-341 (2006).
Hammond et al., A CRISPR-Cas9 gene drive system targeting female reproduction in the malaria mosquito vector Anopheles gambiae. Nat Biotechnol 34, 78-83 (2016).
Hammond et al., The creation and selection of mutations resistant to a gene drive over multiple generations in the malaria mosquito. PLoS Genet 13, e1007039 (2017).
Harris et al., Field performance of engineered male mosquitoes. Nat Biotechnol 29, 1034-1037 (2011).
Harris et al., Successful suppression of a field mosquito population by sustained release of engineered male mosquitoes. Nat Biotechnol 30, 828-830 (2012).
Harvey-Samuel et al., Pest control and resistance management through release of insects carrying a male-selecting transgene. BMC Biol 13, 49 (2015).
Harvey-Samuel et al., Towards the genetic control of invasive species. Biol Invasions 19, 1683-1703 (2017).
Heinrich et al., A repressible female-specific lethal genetic system for making transgenic insect strains suitable for a sterile-release program. Proc Natl Acad Sci U S A 97, 8229-8232 (2000).
Hendrichs, et al., Medfly Areawide Sterile Insect Technique Programmes for Prevention, Suppression or Eradication: the Importance of Mating Behavior Studies, 185 (1), 1-13 223 (2002).
Hsieh et al., A new secreted protein that binds to Wnt proteins and inhibits their activities. Nature 398, 431-436 (1999).
Husken et al., Evaluating biological containment strategies for pollen-mediated gene flow. Environ Biosafety Res 9, 67-73 (2010).
Jia et al., Next-generation CRISPR/Cas9 transcriptional activation in Drosophila using flySAM. Proc Natl Acad Sci U S A 115, 4719-4724 (2018).
Jin et al., Engineered female-specific lethality for control of pest Lepidoptera. ACS Synth Biol 2, 160-166 (2013).
Kalyna et al., Ectopic expression of atRSZ33 reveals its function in splicing and causes pleiotropic changes in development. Mol Biol Cell 14, 3565-3577 (2003).
Kandul et al., Transforming insect population control with precision guided sterile males with demonstration in flies. Nat Commun 10, 84 (2019).
Kaneda et al., The transcription factor OsNAC4 is a key positive regulator of plant hypersensitive cell death. EMBO J 28, 926-936 (2009).
Kiani et al., Cas9 gRNA engineering for genome editing, activation and repression. Nat Methods 12, 1051-1054 (2015).
Kim et al., Overexpression of wound-responsive RNA-binding proteins induces leaf senescence and hypersensitive-like cell death. New Phytol 180, 57-70 (2008).
Konermann et al., Genome-scale transcriptional activation by an engineered CRISPR-Cas9 complex. Nature 517, 583-588 (2015).
Kraemer et al., The global distribution of the arbovirus vectors Aedes aegypti and Ae. albopictus. Elife 4, e08347 (2015).
Lajoie et al., Genomically recoded organisms expand biological functions. Science 342, 357-360 (2013).
Leclere et al., A library of Arabidopsis 35S-cDNA lines for identifying novel mutants. Plant Molecular Biology (2001) 46: 695-703.
Legros et al., Evaluation of location-specific predictions by a detailed simulation model of Aedes aegypti populations. PLoS One 6, e22701 (2011).
Li et al., CRISPR/Cas9-mediated mutagenesis of the white and Sex lethal loci in the invasive pest, Drosophila suzukii. Biochem Biophys Res Commun 469, 911-916 (2016).
Li et al., Transgenic sexing system for genetic control of the Australian sheep blow fly Lucilia cuprina. Insect Biochem Mol Biol 51, 80-88 (2014).
Lin et al., In Vivo Transcriptional Activation Using CRISPR/Cas9 in Drosophila. Genetics 201, 433-442 (2015).
Liu et al., Construction of a GAL1-regulated yeast cDNA expression library and its application to the identification of genes whose overexpression causes lethality in yeast. Genetics 132, 665-673 (1992).
Lowder et al., A CRISPR/Cas9 Toolbox for Multiplexed Plant Genome Editing and Transcriptional Regulation. Plant Physiol 169, 971-985 (2015).
Luo et al., 'GM-gene-deletor': fused loxP-FRT recognition sequences dramatically improve the efficiency of FLP or CRE recombinase on transgene excision from pollen and seed of tobacco plants. Plant Biotechnol J 5, 263-274 (2007).
Magori et al., Skeeter Buster: a stochastic, spatially explicit modeling tool for studying Aedes aegypti population replacement and population suppression strategies. PLoS Negl Trop Dis 3, e508 (2009).
Marshall et al., Confinement of gene drive systems to local populations: a comparative analysis. J Theor Biol 294, 153-171 (2012).
Marshall et al., Overcoming evolved resistance to population-suppressing homing-based gene drives. Sci Rep 7, 3776 (2017).
Maselko et al., Engineering species-like barriers to sexual reproduction. Nat Commun 8, 883 (2017).
Maselko, "Genetic incompatibility combined with female-lethality is effective and robust in simulations of Aedes aegypti population control" Preprint May 2018; DOI: 10.1101/316406.

(56) References Cited

OTHER PUBLICATIONS

Mohanty et al., Wolbachia: A biological control strategy against arboviral diseases. J Vector Borne Dis 53, 199-207 (2016).
Moreno, "Design and Construction of Synthetic Species" Jul. 2012 PLOS one, 7(7): e39054.
Muller et al. Isolating mechanisms, evolution and temperature. Biol. Symp 6, 71-125 (1942).
Murphy, "Improving containment strategies in biopharming" Sep. 2007 Plant Biotechnol J., 5(5):555-69.
Nash et al., Isolation and characterization of WHI3, a size-control gene of *Saccharomyces cerevisiae*. Genetics 157, 1469-1480 (2001).
Navarro, Gene drive in *Drosophilamelanogaster* and Aedes aegypti. Doctoral thesis (online). Cardiff Univeristy. Sep. 2017 [retrieved on Jan. 4, 2021].
Neff et al., Isolation of the beta-tubulin gene from yeast and demonstration of its essential function in vivo. Cell 33, 211-219 (1983).
Noble et al. Current CRISPR gene drive systems are likely to be highly invasive in wild populations. bioRxiv 219022 (2017).
Novitski et al., The entire compound autosomes of *Drosophila melanogaster*. Genetics 98, 257-273 (1981).
Orr et al., The evolution of postzygotic isolation: accumulating Dobzhansky-Muller incompatibilities. Evolution 55, 1085-1094 (2001).
Otte et al., Erv41p and Erv46p: new components of COPII vesicles involved in transport between the ER and Golgi complex. J Cell Biol 152, 503-518 (2001).
Oye et al., Biotechnology. Regulating gene drives. Science 345, 626-628 (2014).
Pfeiffer et al., Refinement of tools for targeted gene expression in *Drosophila*. Genetics 186, 735-755 (2010).
Pfeiffer et al., Using translational enhancers to increase transgene expression in *Drosophila*. Proc Natl Acad Sci U S A 109, 6626-6631 (2012).
Prelich, Gene Overexpression: Uses, Mechanisms, and Interpretation. Genetics (2012), 190: 841-954.
Presgraves, The molecular evolutionary basis of species formation. Nat Rev Genet 11, 175-180 (2010).
Reeves et al., First steps towards underdominant genetic transformation of insect populations, PLoS One 9, e97557 (2014).
Rendon et al., Medfly (Diptera: Tephritidae) genetic sexing: large-scale field comparison of males-only and bisexual sterile fly releases in Guatemala. J Econ Entomol 97, 1547-1553 (2004).
Richardson et al., Enhancing homology-directed genome editing by catalytically active and inactive CRISPR-Cas9 using asymmetric donor DNA. Nat Biotechnol 34, 339-344 (2016).
Robert et al., A reduce and replace strategy for suppressing vector-borne diseases: insights from a deterministic model. PLoS One 8, e73233 (2013).
Rorth, A modular misexpression screen in *Drosophila* detecting tissue-specific phenotypes. Proc Natl Acad Sci U S A 93, 12418-12422 (1996).
Rother et al., Swt1, a novel yeast protein, functions in transcription. J Biol Chem 281, 36518-36525 (2006).
Rovner et al., Recoded organisms engineered to depend on synthetic amino acids. Nature 518, 89-93 (2015).
Ryffel, Transgene flow: Facts, speculations and possible countermeasures. GM Crops & Food (2014), 5(4): 249-258.
Schetelig et al., Site-specific recombination for the modification of transgenic strains of the Mediterranean fruit fly *Ceratitis capitata*. Proc Natl Acad Sci U S A 106, 18171-18176 (2009).
Sheppard et al. The Dynamics of an Adult Population of Aedes aegypti in Relation to Dengue Haemorrhagic Fever in Bangkok. J. Anim. Ecol. 38, 661-702 (1969).
Shockett et al., A modified tetracycline-regulated system provides autoregulatory, inducible gene expression in cultured cells and transgenic mice. Proc Natl Acad Sci U S A 92, 6522-6526 (1995).
Sinkins et al., Gene drive systems for insect disease vectors. Nat Rev Genet 7, 427-435 (2006).
Skruzny et al., An endoribonuclease functionally linked to perinuclear mRNP quality control associates with the nuclear pore complexes. PLoS Biol 7, e8 (2009).
Smanski et al., Genetic manipulation of sex ratio in mammals: the Reaper comes for Mickey. EMBO Rep 20, e48577 (2019).
Sopko et al., Mapping pathways and phenotypes by systematic gene overexpression. Mol Cell 21, 319-330 (2006).
Storici et al., Delitto perfetto targeted mutagenesis in yeast with oligonucleotides. Genet Eng (N Y) 25, 189-207 (2003).
Stuurman et al., Ectopic overexpression of *Drosophila lamin* C is stage-specific lethal. Experimental Cell Research (1999) 248(2):350-357.
Szabad et al., An assay to detect in vivo Y chromosome loss in *Drosophila* wing disc cells. G3 (Bethesda) 2, 1095-1102 (2012).
Tan et al., Transgene-based, female-specific lethality system for genetic sexing of the silkworm, *Bombyx mori*. Proc Natl Acad Sci U S A 110, 6766-6770 (2013).
Teixeira et al., The YEASTRACT database: an upgraded information system for the analysis of gene and genomic transcription regulation in *Saccharomyces cerevisiae*. Nucleic Acids Res 42, D161-166 (2014).
Thailayil et al., Spermless males elicit large-scale female responses to mating in the malaria mosquito *Anopheles gambiae*. Proc Natl Acad Sci U S A 108, 13677-13681 (2011).
Thomas et al., Insect population control using a dominant, repressible, lethal genetic system. Science 287, 2474-2476 (2000).
Thresher et al. Sex-ratio-biasing constructs for the control of invasive lower vertebrates. Nat. Biotechnol. 32, 424-427 (2014).
Turelli et al., Theory and speciation. Trends Ecol Evol 16, 330-343 (2001).
Van Dijken et al., An interlaboratory comparison of physiological and genetic properties of four *Saccharomyces cerevisiae* strains. Enzyme Microb Technol 26, 706-714 (2000).
Vargas-Teran et al., Impact of Screwworm Eradication 217 Programmes Using the Sterile Insect Technique. in Sterile Insect Technique 629-650 218 (Springer-Verlag, 2005). doi: 10.1007/1-4020-4051-2_24.
Waters et al., Rationally-engineered reproductive barriers using CRISPR & CRISPRa: an evaluation of the synthetic species concept in *Drosophila melanogaster*. Sci Rep 8, 13125 (2018).
Wise De Valdez et al., Genetic elimination of dengue vector mosquitoes. Proc Natl Acad Sci U S A 108, 4772-4775 (2011).
Wodarz, Molecular control of cell polarity and asymmetric cell division in *Drosophila* neuroblasts. Current Opinion in Cell Biology (2005) 17(5): 475-481.
Wong et al., Production of reproductively sterile fish: A mini-review of germ cell elimination technologies. General and Comparative Endocrinology (2015), 221: 3-8.
Wright et al., Characterization of COX9, the nuclear gene encoding the yeast mitochondrial protein cytochrome c oxidase subunit VIIa. Subunit VIIa lacks a leader peptide and is an essential component of the holoenzyme. J Biol Chem 261, 17183-17191 (1986).
Wyss, Screwworm eradication in the Americas. Ann N Y Acad Sci 916, 186-193 (2000).
Yan et al., Building early-larval sexing systems for genetic control of the Australian sheep blow fly *Lucilia cuprina* using two constitutive promoters. Sci Rep 7, 2538 (2017).
Yoshida et al., superwoman1-cleistogamy, a hopeful allele for gene containment in GM rice. Plant Biotechnol J 5, 835-846 (2007).
Zabalou et al., Wolbachia-induced cytoplasmic incompatibility as a means for insect pest population control. Proc Natl Acad Sci U S A 101, 15042-15045 (2004).
Zalatan et al., Engineering complex synthetic transcriptional programs with CRISPR RNA scaffolds. Cell 160, 339-350 (2015).
Zhang et al., Mapping of transcription start sites in *Saccharomyces cerevisiae* using 5' SAGE. Nucleic Acids Res 33, 2838-2851 (2005).

\* cited by examiner

SEQUENCE LISTING

<160> NUMBER OF SEQ ID NOS: 6

<210> SEQ ID NO 1
<211> LENGTH: 4335
<212> TYPE: DNA
<213> ORGANISM: artificial
<220> FEATURE:
<223> OTHER INFORMATION: plasmid

<400> SEQUENCE: 1
catagcttca aaatgtttct actccttttt tactcttcca gattttctcg gactccgcgc        60
atcgccgtac cacttcaaaa cacccaagca cagcatacta aatttcccct ctttcttcct       120
ctagggtgtc gttaattacc cgtactaaag gtttggaaaa gaaaaaagag gccgcctcgt       180
ttctttttct tcgtcgaaaa aggcaataaa aatttttatc acgtttcttt ttcttgaaaa       240
tttttttttt gattttttc tctttcgatg acctcccatt gatatttaag ttaataaacg       300
gtcttcaatt tctcaagttt cagtttcatt tttcttgttc tattacaact ttttttactt       360
cttgctcatt agaaagaaag catagcaatc taatctaagt tttctagatg gcttcaaact       420
ttactcagtt cgtgctcgtg gacaatggtg ggacagggga tgtgacagtg gctccttcta       480
atttcgctaa tggggtggca gagtggatca gctccaactc acgagccag gcctacaagg       540 tgacatgcag cgtcaggcag tctagtgccc agaagagaaa gtataccatc aaggtggagg       600
tccccaaagt ggctacccag acagtgggcg gagtcgaact gcctgtcgcc gcttggaggt       660
cctacctgaa catggagctc actatcccaa ttttcgctac caattctgac tgtgaactca       720
tcgtgaaggc aatgcagggg ctcctcaaag acggtaatcc tatcccttcc gccatcgccg       780
ctaactcagg tatctacagc gctggaggag gtggaagcgg aggaggagga agcggaggag       840
gaggtagcgg acctaagaaa aagaggaagg tggcggccgc tggttccgga cgggctgacg       900
cattggacga ttttgatctg gatatgctgg gaagtgacgc cctcgatgat tttgaccttg       960
acatgcttgg ttcggatgcc cttgatgact ttgacctcga catgctcggc agtgacgccc      1020
ttgatgattt cgacctggac atgctgatta actctagatg agcggatctc ttatgtcttt      1080
acgatttata gttttcatta tcaagtatgc ctatattagt atatagcatc tttagatgac      1140
agtgttcgaa gtttcacgaa taaagataa tattctactt tttgctccca ccgcgtttgc      1200
tagcacgagt gaacaccatc cctcgcctgt gagttgtacc cattcctcta aactgtagac      1260
atggtagctt cagcagtgtt cgttatgtac ggcatcctcc aacaaacagt cggttatagt      1320
ttgtcctgct cctctgaatc gagtccctcg atatttctca tactagttct agagatcgag      1380
ctcgttttcg acactggatg gcggcgttag tatcgaatcg acagcagtat agcgaccagc      1440
attcacatac gattgacgca tgatattact ttctgcgcac ttaacttcgc atctgggcag      1500
atgatgtcga ggcgaaaaaa aatataaatc acgctaacat ttgattaaaa tagaacaact      1560
acaatataaa aaaactatac aaatgacaag ttcttgaaaa caagaatctt tttattgtca      1620

```
gtactgatta gaaaaactca tcgagcatca aatgaaactg caatttattc atatcaggat    1680
tatcaatacc atattttttga aaaagccgtt tctgtaatga aggagaaaac tcaccgaggc    1740
```

```
gtactgatta gaaaaactca tcgagcatca aatgaaactg caatttattc atatcaggat    1680
tatcaatacc atattttga  aaaagccgtt tctgtaatga aggagaaaac tcaccgaggc    1740
agttccatag gatggcaaga tcctggtatc ggtctgcgat tccgactcgt ccaacatcaa    1800
tacaacctat taatttcccc tcgtcaaaaa taaggttatc aagtgagaaa tcaccatgag    1860
tgacgactga atccggtgag aatggcaaaa gcttatgcat ttctttccag acttgttcaa    1920
caggccagcc attacgctcg tcatcaaaat cactcgcatc aaccaaaccg ttattcattc    1980
gtgattgcgc ctgagcgaga cgaaatacgc gatcgctgtt aaaaggacaa ttacaaacag    2040
gaatcgaatg caaccggcgc aggaacactg ccagcgcatc aacaatattt tcacctgaat    2100
caggatattc ttctaatacc tggaatgctg ttttgccggg gatcgcagtg gtgagtaacc    2160
atgcatcatc aggagtacgg ataaaatgct tgatggtcgg aagaggcata aattccgtca    2220
gccagtttag tctgaccatc tcatctgtaa catcattggc aacgctacct ttgccatgtt    2280
tcagaaacaa ctctggcgca tcgggcttcc catacaatcg atagattgtc gcacctgatt    2340
gcccgacatt atcgcgagcc catttatacc catataaatc agcatccatg ttggaattta    2400
atcgcggcct cgaaacgtga gtcttttcct tacccatggt tgcgaattga tccggtaatt    2460
tagtgtgtgt atttgtgttt gcgtgtctat agaagtatag taatttatgc tacaaaggac    2520
ctaatgtata aggaaagaat atttagagaa aagaagaaaa caagagtttt atatacatac    2580
agagcacatg catgccatat tttatttatg caagaggacg tggtccttca aatatgtatc    2640
cgctcatgag acaataaccc tgataaatgc ttcaataata ttgaaaaagg aagagtatga    2700
gtattcaaca tttccgtgtc gcccttattc ccttttttgc ggcattttgc cttcctgttt    2760
ttgctcaccc agaaacgctg gtgaaagtaa aagatgctga agatcagttg ggtgcacgag    2820
tgggttacat cgaactggat ctcaacagcg gtaagatcct tgagagtttt cgccccgaag    2880
aacgttttcc aatgatgagc acttttaaag ttctgctatg tggcgcggta ttatcccgta    2940
ttgacgccgg gcaagagcaa ctcggtcgcc gcatacacta ttctcagaat gacttggttg    3000
agtactcacc agtcacagaa aagcatctta cggatggcat gacagtaaga gaattatgca    3060
gtgctgccat aaccatgagt gataacactg cggccaactt acttctgaca acgatcggag    3120
gaccgaagga gctaaccgct tttttgcaca acatggggga tcatgtaact cgccttgatc    3180
gttgggaacc ggagctgaat gaagccatac caaacgacga gcgtgacacc acgatgcctg    3240
tagcaatggc aacaacgttg cgcaaactat taactggcga actacttact ctagcttccc    3300
ggcaacaatt aatagactgg atggaggcgg ataaagttgc aggaccactt ctgcgctcgg    3360
cccttccggc tggctggttt attgctgata aatctggagc cggtgagcgt ggctctcgcg    3420
gtatcattgc agcactgggg ccagatggta agccctcccg tatcgtagtt atctacacga    3480
cggggagtca ggcaactatg gatgaacgaa atagacagat cgctgagata ggtgcctcac    3540
tgattaagca ttggtaactg tcagaccaag tttactcata tatactttag attgatttaa    3600
aacttcattt ttaatttaaa aggatctagg tgaagatcct ttttgataaa tgggccgcgt    3660
tgctggcgtt tttccatagg ctccgccccc ctgacgagca tcacaaaaat cgacgctcaa    3720
gtcagaggtg cgaaacccg acaggactat aaagatacca ggcgtttccc cctggaagct    3780
ccctcgtgcg ctctcctgtt ccgaccctgc cgcttaccgg atacctgtcc gcctttctcc    3840
cttcgggaag cgtggcgctt tctcatagct cacgctgtag gtatctcagt tcggtgtagg    3900
tcgttcgctc caagctgggc tgtgtgcacg aaccccccgt tcagcccgac cgctgcgcct    3960
tatccggtaa ctatcgtctt gagtccaacc cggtaagaca cgacttatcg ccactggcag    4020
```

```
cagccactgg taacaggatt agcagagcga ggtatgtagg cggtgctaca gagttcttga    4080
agtggtggcc taactacggc tacactagaa gaacagtatt tggtatctgc gctctgctga    4140
agccagttac cttcggaaaa agagttggta gctcttgatc cggcaaacaa accaccgctg    4200
gtagcggtgg tttttttgtt tgcaagcagc agattacgcg cagaaaaaaa ggatctcaag    4260
aagatccttt gatcttttct acggggtctg acgctcagtg gaacgaaaac tcacgttaag    4320
ggattttggt catga                                                     4335

<210> SEQ ID NO 2
<211> LENGTH: 4332
<212> TYPE: DNA
<213> ORGANISM: artificial
<220> FEATURE:
<223> OTHER INFORMATION: plasmid

<400> SEQUENCE: 2
catagcttca aaatgtttct actccttttt tactcttcca gattttctcg gactccgcgc      60
atcgccgtac cacttcaaaa cacccaagca cagcatacta aatttcccct ctttcttcct     120
ctagggtgtc gttaattacc cgtactaaag gtttggaaaa gaaaaaagag gccgcctcgt     180 ttcttttttct tcgtcgaaaa aggcaataaa aatttttatc acgtttcttt tcttgaaaa     240 tttttttttt gattttttttc tctttcgatg acctcccatt gatatttaag ttaataaacg     300
gtcttcaatt tctcaagttt cagtttcatt tttcttgttc tattacaact ttttttactt     360
cttgctcatt agaaagaaag catagcaatc taatctaagt tttctagatg gcttcaaact     420
ttactcagtt cgtgctcgtg gacaatggtg ggacagggga tgtgacagtg gctccttcta     480
atttcgctaa tggggtggca gagtggatca gctccaactc acggagccag gcctacaagg     540
tgacatgcag cgtcaggcag tctagtgccc agaagagaaa gtataccatc aaggtggagg     600
tccccaaagt ggctacccag acagtgggcg gagtcgaact gcctgtcgcc gcttggaggt     660
cctacctgaa catggagctc actatcccaa ttttcgctac caattctgac tgtgaactca     720
tcgtgaaggc aatgcagggg ctcctcaaag acggtaatcc tatcccttcc gccatcgccg     780
ctaactcagg tatctacagc gctggaggag gtggaagcgg aggaggagga agcggaggag     840
gaggtagcgg acctaagaaa agaggaaggt tggcggccgc tggttccgga cgggctgacg     900
cattggacga ttttgatctg gatatgctgg gaagtgacgc cctcgatgat ttgaccttg     960 acatgcttgg ttcggatgcc cttgatgact tgacctcga catgctcggc agtgacgccc    1020
ttgatgattt cgacctggac atgctgatta actctagatg agcggatctc ttatgtcttt    1080
acgatttata gttttcatta tcaagtatgc ctatattagt atatagcatc tttagatgac    1140
agtgttcgaa gtttcacgaa taaagataaa tattctactt tttgctccca ccgcgtttgc    1200
tagcacgagt gaacaccatc cctcgcctgt gagttgtacc cattcctcta aactgtagac    1260
atggtagctt cagcagtgtt cgttatgtac ggcatcctcc aacaaacagt cggttatagt    1320
ttgtcctgct cctctgaatc gagtccctcg atatttctca tactagttct agagatcgag    1380
ctcgttttcg acactggatg gcggcgttag tatcgaatcg acagcagtat agcgaccagc    1440
attcacatac gattgacgca tgatattact ttctgcgcac ttaacttcgc atctgggcag    1500
atgatgtcga ggcgaaaaaa aatataaatc acgctaacat tgattaaaa tagaacaact    1560 acaatataaa aaaactatac aaatgacaag ttccttgaaaa caagaatctt tttattgtca    1620
gtactgatta gaaaaactca tcgagcatca aatgaaactg caatttattc atatcaggat    1680
```

```
tatcaatacc atattttga aaaagccgtt tctgtaatga aggagaaaac tcaccgaggc    1740
agttccatag gatggcaaga tcctggtatc ggtctgcgat tccgactcgt ccaacatcaa    1800
tacaacctat taatttcccc tcgtcaaaaa taaggttatc aagtgagaaa tcaccatgag    1860
tgacgactga atccggtgag aatggcaaaa gctttatgcat ttctttccag acttgttcaa    1920
caggccagcc attacgctcg tcatcaaaat cactcgcatc aaccaaaccg ttattcattc    1980
gtgattgcgc ctgagcgaga cgaaatacgc gatcgctgtt aaaaggacaa ttacaaacag    2040
gaatcgaatg caaccggcgc aggaacactg ccagcgcatc aacaatattt tcacctgaat    2100
caggatattc ttctaatacc tggaatgctg ttttgccggg gatcgcagtg gtgagtaacc    2160
atgcatcatc aggagtacgg ataaaatgct tgatggtcgg aagaggcata aattccgtca    2220
gccagtttag tctgaccatc tcatctgtaa catcattggc aacgctacct ttgccatgtt    2280
tcagaaacaa ctctggcgca tcgggcttcc catacaatcg atagattgtc gcacctgatt    2340
gcccgacatt atcgcgagcc catttatacc catataaatc agcatccatg ttggaattta    2400
atcgcggcct cgaaacgtga gtcttttcct tacccatggt tgcgaattga tccggtaatt    2460
tagtgtgtgt atttgtgttt gcgtgtctat agaagtatag taatttatgc tacaaaggac    2520
ctaatgtata aggaaagaat atttagagaa aagaagaaaa caagagtttt atatacatac    2580
agagcacatg catgccatat tgtgaagagt cttatacagt tccttcaaat atgtatccgc    2640
tcatgagaca ataaccctga taaatgcttc aataatattg aaaaggaag agtatgagta    2700 ttcaacattt ccgtgtcgcc cttattccct ttttttgcggc attttgcctt cctgtttttg    2760
ctcacccaga aacgctggtg aaagtaaaag atgctgaaga tcagttgggt gcacgagtgg    2820
gttacatcga actggatctc aacagcggta agatccttga gttttcgc cccgaagaac    2880 gttttccaat gatgagcact tttaaagttc tgctatgtgg cgcggtatta tcccgtattg    2940
acgccgggca agagcaactc ggtcgccgca tacactattc tcagaatgac ttggttgagt    3000
actcaccagt cacagaaaag catcttacgg atggcatgac agtaagagaa ttatgcagtg    3060
ctgccataac catgagtgat aacactgcgg ccaacttact tctgacaacg atcggaggac    3120
cgaaggagct aaccgctttt ttgcacaaca tgggggatca tgtaactcgc cttgatcgtt    3180
gggaaccgga gctgaatgaa gccataccaa acgacgagcg tgacaccacg atgcctgtag    3240
caatggcaac aacgttgcgc aaactattaa ctggcgaact acttactcta gcttcccggc    3300
aacaattaat agactggatg gaggcggata agttgcagg accacttctg cgctcggccc    3360
ttccggctgg ctggtttatt gctgataaat ctggagccgg tgagcgtggc tctcgcggta    3420
tcattgcagc actggggcca gatggtaagc cctcccgtat cgtagttatc tacacgacgg    3480
ggagtcaggc aactatggat gaacgaaata gacagatcgc tgagataggt gcctcactga    3540
ttaagcattg gtaactgtca gaccaagttt actcatatat actttagatt gatttaaaac    3600 ttcatttta atttaaaagg atctaggtga agatccttt tgataaatgg gccgcgttgc    3660
tggcgttttt ccataggctc cgcccccctg acgagcatca caaaaatcga cgctcaagtc    3720
agaggtggcg aaacccgaca ggactataaa gataccaggc gtttccccct ggaagctccc    3780
tcgtgcgctc tcctgttccg accctgccgc ttaccggata cctgtccgcc tttctccctt    3840
cgggaagcgt ggcgctttct catagctcac gctgtaggta tctcagttcg gtgtaggtcg    3900
ttcgctccaa gctgggctgt gtgcacgaac cccccgttca gcccgaccgc tgcgccttat    3960
ccggtaacta tcgtcttgag tccaacccgg taagacacga cttatcgcca ctggcagcag    4020
ccactggtaa caggattagc agagcgaggt atgtaggcgg tgctacagag ttcttgaagt    4080
```

```
ggtggcctaa ctacggctac actagaagaa cagtatttgg tatctgcgct ctgctgaagc    4140
cagttacctt cggaaaaaga gttggtagct cttgatccgg caaacaaacc accgctggta    4200
gcggtggttt ttttgtttgc aagcagcaga ttacgcgcag aaaaaaagga tctcaagaag    4260
atcctttgat cttttctacg gggtctgacg ctcagtggaa cgaaaactca cgttaaggga    4320
ttttggtcat ga                                                        4332

<210> SEQ ID NO 3
<211> LENGTH: 72
<212> TYPE: DNA
<213> ORGANISM: artificial
<220> FEATURE:
<223> OTHER INFORMATION: primer

<400> SEQUENCE: 3
ggcatcgcac agttttagcg aggaaaactc ttcaatagtt ttgccagcgg catagcttca    60
aaatgtttct ac                                                        72

<210> SEQ ID NO 4
<211> LENGTH: 70
<212> TYPE: DNA
<213> ORGANISM: artificial
<220> FEATURE:
<223> OTHER INFORMATION: primer

<400> SEQUENCE: 4
aattcatatt taattattgt acatggacat atcatacgta atgctcaacc gagcggatac    60
atatttgaag                                                           70

<210> SEQ ID NO 5
<211> LENGTH: 23
<212> TYPE: DNA
<213> ORGANISM: artificial
<220> FEATURE:
<223> OTHER INFORMATION: plasmid

<400> SEQUENCE: 5
ccacgtcctc ttgcataaat aaa                                            23

<210> SEQ ID NO 6
<211> LENGTH: 20
<212> TYPE: DNA
<213> ORGANISM: artificial
<220> FEATURE:
<223> OTHER INFORMATION: plasmid

<400> SEQUENCE: 6
actgtataag actcttcaca                                                20
```

PROGRAMMABLE TRANSCRIPTION FACTORS AND METHODS

CROSS-REFERENCE TO RELATED APPLICATION

This application is the § 371 U.S. National Stage of International Application No. PCT/US2018/031950, filed May 10, 2018, which claims priority to U.S. Provisional Patent Application No. 62/504,260, filed May 10, 2017, each of which is incorporated herein by reference in its entirety.

SEQUENCE LISTING

This application contains a Sequence Listing electronically submitted via EFS-Web to the United States Patent and Trademark Office as an ASCII text file entitled "SequenceListing11005750201_ST25.txt" having a size of 16 kilobytes and created on May 9, 2018. The information contained in the Sequence Listing is incorporated by reference herein.

SUMMARY

This disclosure describes, in one aspect, a programmable transcription activator system. Generally, the system includes a programmable transcription activator, a polynucleotide that includes a coding region whose expression is required for cell viability, and a promoter operably linked to the polynucleotide and having a binding site for the programmable transcription activator. The programmable transcription activator generally includes a domain that specifically binds to a promoter and a transcriptional activator domain.

In some embodiments, the promoter may be operably linked to at least one additional coding region that is not essential for cell viability. The non-essential coding region may be under transcriptional control of the promoter sequence that controls expression of the essential coding region. Alternatively, the non-essential coding region may be under transcriptional control of a second copy of the promoter sequence that controls expression of the essential coding region.

In some embodiments, the non-essential coding region encodes a polypeptide involved in cell growth, cell reproduction, producing a secondary metabolite, or modulating an immune response.

In another aspect, this disclosure describes a programmable transcription repressor system. Generally, the system includes a programmable transcription repressor, a polynucleotide that includes a coding region whose expression is toxic to cell viability, and a promoter operably linked to the polynucleotide and having a binding site for the programmable transcription repressor. The programmable transcription repressor generally includes a domain that specifically binds to a promoter and a transcriptional repressor domain.

In some embodiments, the toxic coding region encodes a polypeptide that interferes with cell growth, interferes with central metabolism, interferes with cell reproduction, or interferes with an immune response.

In some embodiments, the promoter may be operably linked to at least one additional coding region that is not essential for cell viability. The non-essential coding region may be under transcriptional control of the promoter sequence that controls expression of the essential coding region. Alternatively, the non-essential coding region may be under transcriptional control of a second copy of the promoter sequence that controls expression of the essential coding region.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. Programmable-transcription-activator-dependent survival of host cell. (A) Schematics of tester plasmid (top) and control plasmid (bottom) The tester plasmid contains a minimal promoter, a dCas9-VP64 targeted sequence, and a KanMX (an aminoglycoside phosphotransferase conferring G418 sulfate resistance) coding region. The control plasmid lacks the dCas9-VP64 targeted sequence. (B) Detail of the KanMX promoter region under the control of a minimal promoter with (top, SEQ ID NO:5) or without (bottom, SEQ ID NO:6) an adjacent dCas9-VP64 targeted sequence. The sequences of SEQ ID NO:5 and SEQ ID NO:6 are shown in the reverse-complement orientation relative to SEQ ID NO:1 and SEQ ID NO:2, respectively. (C) Colony forming results from two independent experiments with yeast expressing dCas9-VP64 and a random or on-target sgRNA transformed with KanMX cassettes with or without a cognate target adjacent to the minimal promoter. (* indicates $p<0.05$, one-way ANOVA followed by Tukey's post-test, n=2 independent transformations, mean+/−SEM)

DETAILED DESCRIPTION OF ILLUSTRATIVE EMBODIMENTS

Programmable transcriptional factors are proteins and/or nucleoproteins that can be used to alter expression of a transcriptional unit. A programmable transcriptional activator such as, for example, dCas9 fused to a transcriptional activator domain (e.g., VP64) or a programmable transcriptional repressor such as, for example, dCas9 fused to a repressor domain (e.g., KRAB) can be used to engineer synthetic transcriptional programs in a wide variety of organisms. These programs may increase production of a high value compound, introduce a block to unwanted geneflow, protect an organism from biotic and/or abiotic stressors, or have other applications.

A programmable transcription factor can be effective if it is functional and present in the cell at a sufficient concentration to affect the desired transcriptional program. Various mutations in a coding region that encodes a component of the programmable transcription factor may interfere with—even eliminate—the function of the programmable transcription factor. Unwanted silencing that reduces or eliminates transcription of the coding region also may interfere with the desired function of the programmable transcription factor. This can be particularly problematic when the programmable transcription factor is expected to function for multiple generations and organisms with defective programmable transcription factors have a growth advantage and may come to dominate the population.

Figure 1:
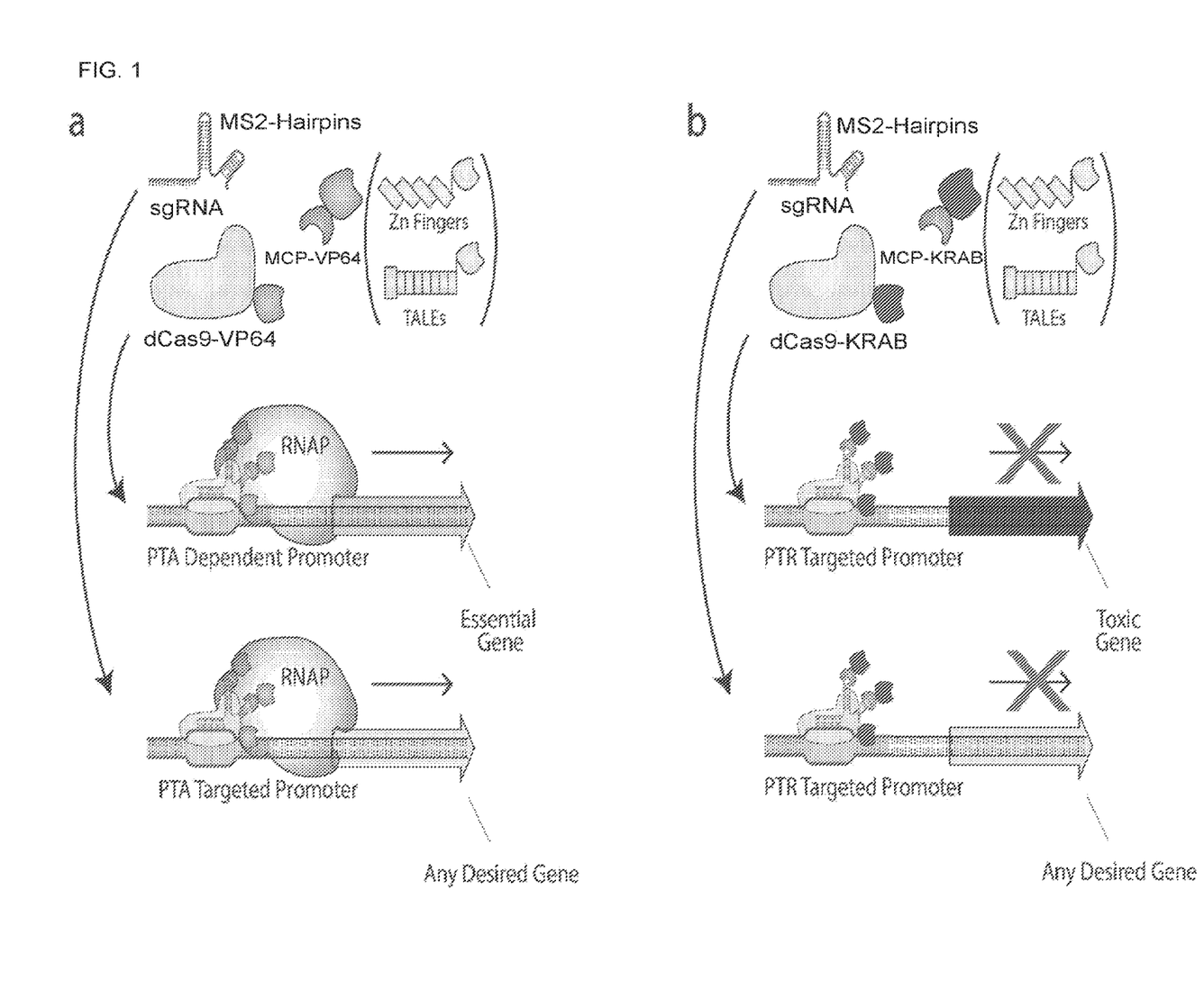
FIG. 1. Overview of positive selection modules. (A) Macromolecular components that constitute programmable transcription activators (top), and schematic illustration showing programmable transcription activator dependent expression of an essential coding region (middle) as well as other desired genes (bottom) using the same target sequence (B) Macromolecular components that constitute programmable transcription repressors (top), and schematic illustration showing repression of a toxic coding region (middle) as well as other desired genes (bottom) using the same target sequence.

This disclosure describes methods and constructs that place programmable transcription factor machinery under positive selection. Organisms that express non-functional or low levels of the programmable transcription factor exhibit poor growth and/or die. This method can be applied to both programmable transcription activators (FIG. 1A) and programmable transcription repressors (FIG. 1B).

In the case of activators, the system includes at least a programmable transcription activator, a coding region whose expression is essential to the survival of the organism, and a promoter controlling the expression of the essential coding region. The promoter binds the programmable transcription activator for expression of the essential coding region that allows the organism to either survive, reproduce, and/or have a normal growth rate. A mutation or silencing in any component of this system has a severely deleterious effect on the organism.

The target sequence of the programmable transcription activator is present in the promoter of the essential coding region and also may be present in the promoter of one or more other coding regions whose transcriptional activation is desirable for some transcriptional program, but may not necessarily be an essential coding region. The essential coding region may encode a polypeptide that is involved in a central metabolic process, growth, reproduction, and/or whose expression is critical in a particular environment, such as a coding region that confers antibiotic or herbicide resistance. Examples of non-essential coding regions includes, for example, those involved in producing secondary metabolites, growth regulators, and/or immune system modulators.

In the case of repressors, the system includes at least a programmable transcription repressor, a coding region whose expression is toxic to the organism, and a sequence within the promoter or coding region of the toxic coding region that requires programmable transcription repressor binding for transcriptional repression to mitigate the effects of the translation product of the toxic coding region. In some cases, it may be possible to target a programmable transcription activator in a way that results in transcriptional repression of the toxic coding region. A mutation or silencing of the programmable transcription repressor or the toxic coding region's programmable transcription repressor binding site is severely deleterious for the organism.

Typically, the target sequence of the programmable transcription repressor is present in the promoter or coding sequence of other coding region(s) whose transcriptional repression is desirable although not necessarily essential for the organism. Examples may include coding regions involved in producing secondary metabolites, growth regulators, and immune system modulators. The toxic coding region may interfere with central metabolism, growth, reproduction, or immune response.

While described herein in the context of an exemplary embodiment in which the programmable transcription activator is dCas9 fused to the activator domain VP64 and co-expressed with MCP-VP64, other programmable transcription activators may be used in the system. Exemplary alternative programmable transcription activators include, for example, fusions of dCas9, dxCas9, Cas9 (if combined with a short guide RNA), nuclease-inactive CPF1, and/or a TALE (e.g., a TALE to VP64, VP16, VPR, p65, Rta, EDLL, Gal4, TV, TAD, or SunTag). Various embodiments of the system can employ two or more programmable transcription activators. In the case of RNA-guided transcriptional regulators (e.g, dCas9-VP64), activation may be boosted by including aptamers in the RNA sequence that recruit aptamer binding protein such as, for example, transcription factor fusions, such as any combination of MS2/MCP, PCP, or COM fused to VP64, VP16, VPR, p65, Rta, EDLL, Gal4, TV or TAD.

Similarly, while described herein in the context of an exemplary embodiment in which the programmable transcription repressor is dCas9 fused to a KRAB domain, other programmable transcription repressors may be used in the system. Exemplary alternative programmable transcription repressors include, for example, fusions of dCas9, dxCas9, Cas9 (if combined with a short guide RNA), nuclease-inactive CPF1, or a TALE fused to NK10, Ubx, REST, Egr-1, Mad, thyroid hormone receptor α, or thyroid hormone receptor β. Other embodiments may repress transcription by binding within the transcribed region of a coding region to interfere with RNA polymerase binding or transcript elongation and may or may not include a fused KRAB domain.

Figure 2:
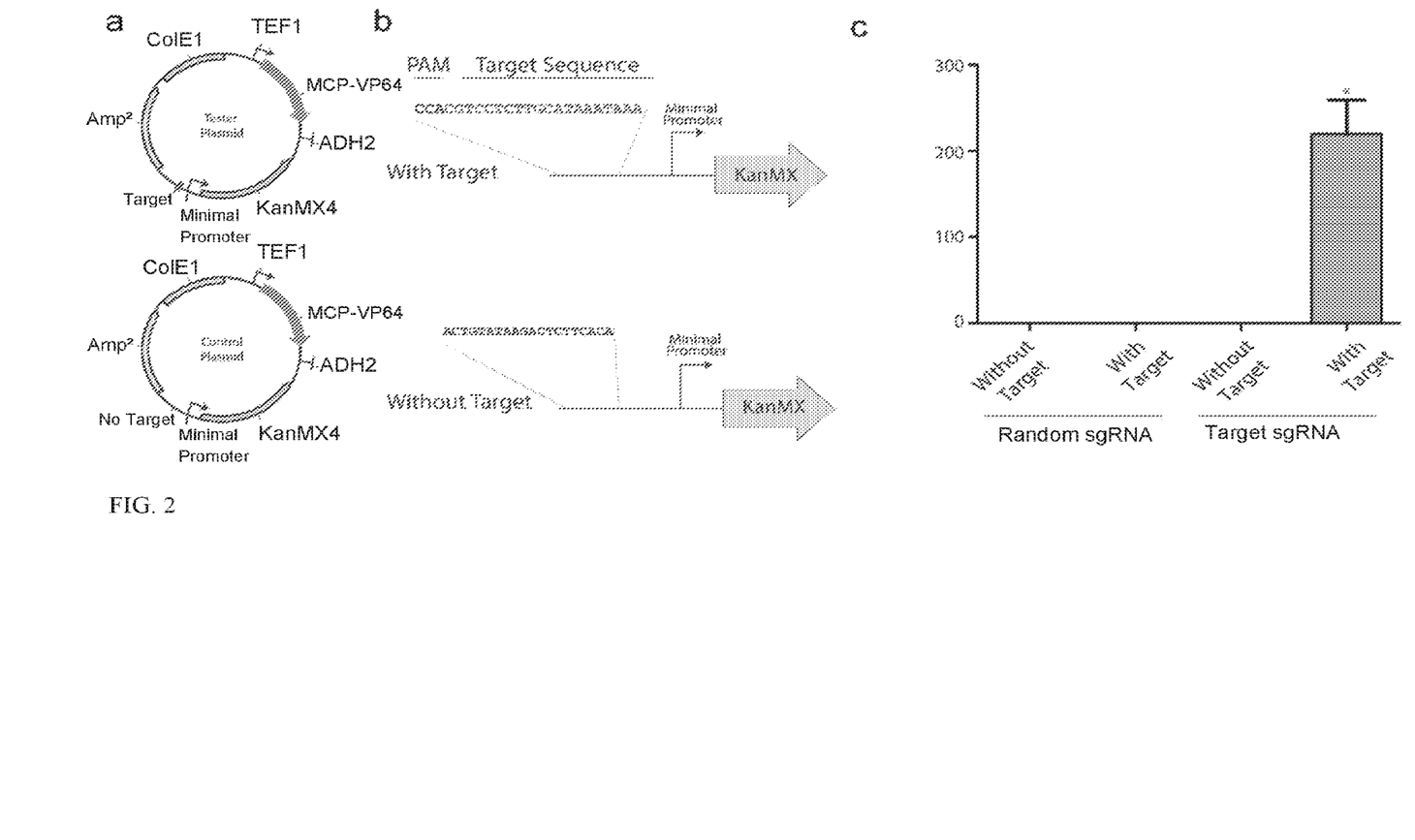

Thus, this disclosure describes a positive selection module using programmable transcription activators in the model host cell, *Saccharomyces cerevisiae* Cen.PK (FIG. 2). A tester plasmid containing the KanMX coding region, which confers resistance to the antibiotic G418 Sulfate, was constructed under the control of a hybrid promoter containing a unique protospacer target sequence upstream of a minimal promoter that included a CYC1 TATA box region. The tester plasmid also contains an MCP-VP64 coding region. A control plasmid without the protospacer sequence also was constructed (FIG. 2A). A PCR product with 5' and 3' ends homologous to the lys2 locus and containing the KanMX and MCP-VP64 coding regions was used in lithium-acetate transformation of yeast strains expressing dCas9-VP64 guided by sgRNA containing MS2 aptamers to recruit MCP-VP64. The sgRNA contained a random targeting sequence or a targeting sequence specific for the protospacer target. Transformed yeast were plated onto YPD media containing 400 µg/ml G418 sulfate. Colonies were only present when the yeast expressed a sgRNA targeting the programmable transcription activator to a target site present in the promoter of KanMX (FIG. 2C). This demonstrates that survival of the yeast in this media was dependent on the activity of the programmable transcription activator.

While described above in the context of an exemplary embodiment in which the host cell is a yeast, *Saccharomyces cerevisiae*, the programmable transcription factors described herein can be introduced into any suitable cell, including the cells of a multicelled organism, where programmable control of transcription is desired. Thus, exemplary alternative hosts for the programmable transcription factors include, for example, plants (e.g., soy, corn, rice, sugar beet) whose herbicide resistance genes (e.g., for glyphosate, bialaphos, dicamba) can be made dependent on the presence of a programmable transcriptional activator; animals (e.g., mosquitoes, fruit flies, rodents, fish, molluscs) whose essential genes (e.g., cell cycle regulators, growth factors, cytoskeletal components) can be made dependent on the presence of a programmable transcriptional activator; or plants, animals, or microbes (e.g., yeast, bacteria, protists), where survival may be made dependent on the expression of a programmable transcriptional repressor preventing the expression of a toxic gene. In the latter case, a toxic gene can be either a foreign gene encoding a toxin or a native gene under the control of an engineered promoter that, when derepressed, drives deleterious overexpression.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

The integration cassettes were PCR amplified with a thermocycler (C1000 Touch, Bio-Rad Laboratories, Inc., Hercules, Calif.) using Q5 polymerase (New England Bio-Labs, Inc., Ipswich, Mass.) from the tester or control plasmid using primers MM_TA_LYS_uF and MM_SGTA_LYS_uR2 with an anneal temperature of 58° C. and an extension time of 2:30.

TABLE 1

| | PCR Primers |
|---|---|
| MM_TA_LYS_uF | GGCATCGCACAGTTTTAGCGAGGAAAACTCTTCAA TAGTTTTGCCAGCGGCATAGCTTCAAAATGTTTCT AC (SEQ ID NO: 3) |
| MM_SGTA_LYS_uR2 | AATTCATATTTAATTATTGTACATGGACATATCAT ACGTAATGCTCAACCgagcggatacatatttgaag (SEQ ID NO: 4) |

The band was gel purified (Zymo Research, Irvine, Calif.) and 300 ng to 500 ng was used for lithium acetate transformation of the yeast. Yeast cells were given a three-hour period of outgrowth at 28° C. before plating on YPD G418 (10 g/L yeast extract, 20 g/L peptone, 20 g/L dextrose, and 400 µg/ml G418 sulfate) and incubating at 28° C. After three days, colonies were counted and normalized to the amount of DNA used in the transformation reactions.

TABLE 2

| Yeast strains used in this study | | |
|---|---|---|
| Name | Genotype[a] | Description |
| YMM130 | MATa ACT1-Δ1 leu2ΔdCas9-VP64 Random sgRNA | Random sgRNA strain. |
| YMM131 | MATa ACT1-Δ1 leu2ΔdCas9-VP64 on target sgRNA | On target sgRNA strain. |

[a]All strains are derived from the CEN.PK background: ura3-52 trp1-289 leu2-3_112 his3 Δ1 MAL2-8C SUC2

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

| Sequence Listing Free Text |
|---|
| Sequence of tester plasmid (SEQ ID NO: 1): CATAGCTTCAAAATGTTTCTACTCCTTTTTTACTCTTCCAGATTTTCTCG GACTCCGCGCATCGCCGTACCACTTCAAAACACCCAAGCACAGCATACTA AATTTCCCCTCTTTCTTCCTCTAGGGTGTCGTTAATTACCCGTACTAAAG GTTTGGAAAAGAAAAAGAGgCCGCCTCGTTTCTTTTTCTTCGTCGAAAA AGGCAATAAAAATTTTTATCACGTTTCTTTTTCTTGAAAATTTTTTTTT GATTTTTTTCTCTTTCGATGACCTCCCATTGATATTTAAGTTAATAAACG GTCTTCAATTTCTCAAGTTTCAGTTTCATTTTTCTTGTTCTATTACAACT TTTTTTACTTCTTGCTCATTAGAAAGAAAGCATAGCAATCTAATCTAAGT TTTCTAGATGGCTTCAAACTTTACTCAGTTCGTGCTCGTGGACAATGGTG GGACAGGGGATGTGACAGTGGCTCCTTCTAATTTCGCTAATGGGGTGGCA GAGTGGATCAGCTCCAACTCACGGAGCCAGGCCTACAAGGTGACATGCAG CGTCAGGCAGTCTAGTGCCCAGAAgAGAAAGTATACCATCAAGGTGGAGG TCCCCAAAGTGGCTACCCAGACAGTGGGCGGAGTCGAACTGCCTGTCGCC |

Sequence Listing Free Text

GCTTGGAGGTCCTACCTGAACATGGAGCTCACTATCCCAATTTTCGCTAC
CAATTCTGACTGTGAACTCATCGTGAAGGCAATGCAGGGGCTCCTCAAAG
ACGGTAATCCTATCCCTTCCGCCATCGCCGCTAACTCAGGTATCTACagc
gctGGAGGAGGTGGAAGCGGAGGAGGAGGAAGCGGAGGAGGAGGTAGCgg
acctaagaaaagaggaaggtggcggccgctGGTTCCGGACGGGCTGACG
CATTGGACGATTTTGATCTGGATATGCTGGGAAGTGACGCCCTCGATGAT
TTTGACCTTGACATGCTTGGTTCGGATGCCCTTGATGACTTTGACCTCGA
CATGCTCGGCAGTGACGCCCTTGATGATTTCGACCTGGACATGCTGATTA
ACTCTAGATGAgcggatctcttatgtctttacgatttatagttttcatta
tcaagtatgcctatattagtatatagcatctttagatgacagtgttcgaa
gtttcacgaataaaagataatattctacttttttgctcccaccgcgtttgc
tagcacgagtgaacaccatccctcgcctgtgagttgtacccattcctcta
aactgtagacatggtagcttcagcagtgttcgttatgtacggcatcctcc
aacaaacagtcggttatagtttgtcctgctcctctgaatcgagtccctcg
atatttctcatactagttctagagatcgagctcgtttttcgacactggatg
gcggcgttagtatcgaatcgacagcagtatagcgaccagcattcacatac
gattgacgcatgatattacttctgcgcacttaacttcgcatctgggcag
atgatgtcgaggcgaaaaaaatataaatcacgctaacatttgattaaaa
tagaacaactacaatataaaaaaactatacaaatgacaagttcttgaaaa
caagaatcttttttattgtcagtactgattagaaaaactcatcgagcatca
aatgaaactgcaatttattcatatcaggattatcaataccatatttttga
aaaagccgtttctgtaatgaaggagaaaactcaccgaggcagttccatag
gatggcaagatcctggtatcggtctgcgattccgactcgtccaacatcaa
tacaacctattaatttccccctcgtcaaaaataaggttatcaagtgagaaa
tcaccatgagtgacgactgaatccggtgagaatggcaaaagcttatgcat
ttctttccagacttgttcaacaggccagccattacgctcgtcatcaaaat
cactcgcatcaaccaaaccgttattcattcgtgattgcgcctgagcgaga
cgaaatacgcgatcgctgttaaaaggacaattacaaacaggaatcgaatg
caaccggcgcaggaacactgccagcgcatcaacaatatttcacctgaat
caggatattcttctaatacctggaatgctgttttgccggggatcgcagtg
gtgagtaaccatgcatcatcaggagtacggataaaatgcttgatggtcgg
aagaggcataaattccgtcagccagtttagtctgaccatctcatctgtaa
catcattggcaacgctaccttttgccatgtttcagaaacaactctggcgca
tcgggcttcccatacaatcgatagattgtcgcacctgattgcccgacatt
atcgcgagcccatttataccatataaatcagcatccatgttggaattta
atcgcggcctcgaaacgtgagtcttttccttacccatggttgcgaattga
tccggtaatttagtgtgtgtatttgtgtttgcgtgtctatagaagtatag
taatttatgctacaaaggacctaatgtataaggaaagaatatttagagaa
aagaagaaaacaagagttttatatacatacagagcacatgcatgccataT
TTTATTTATGCAAGAGGACGTGGTCCTtcaaatatgtatccgctcatgag
acaataaccctgataaatgcttcaataatattgaaaaaggaagagtatga
gtattcaacatttccgtgtcgcccttattcccttttttgcggcattttgc
cttcctgtttttgctcacccagaaacgctggtgaaagtaaaagatgctga
agatcagttgggtgcacgagtgggttacatcgaactggatctcaacagcgta
gtaagatccttgagagttttcgccccgaagaacgttttccaatgatgagc
acttttaaagttctgctatgtggcgcggtattatcccgtattgacgccgg
gcaagagcaactcggtcgccgcatacactattctcagaatgacttggttg
agtactcaccagtcacagaaaagcatcttacggatggcatgacagtaaga
gaattatgcagtgctgccataaccatgagtgataacactgcggccaactt
acttctgacaacgatcggaggaccgaaggagctaaccgcttttttgcaca
acatggggatcatgtaactcgccttgatcgttgggaaccggagctgaat
gaagccataccaaacgacgagcgtgacaccacgatgcctgtagcaatggc
aacaacgttgcgcaaactattaactggcgaactacttactctagcttccc
ggcaacaattaatagactggatggaggcggataaagttgcaggaccacttctg
ctgcgctcggcccttccggctggctggtttattgctgataaatctggagc
cggtgagcgtggctctcgcggtatcattgcagcactggggccagatggta
agccctcccgtatcgtagttatctacacgacggggagtcaggcaactatg
gatgaacgaaatagacagatcgctgagataggtgcctcactgattaagca
ttggtaactgtcagaccaagtttactcatatatactttagattgatttaa
aactttcatttttaatttaaaaggatctaggtgaagatcctttttgataaa
tgggcctgttgctggcttttttccataggctccgcccccctgacgagcaa
tcacaaaaatcgacgctcaagtcagaggtggcgaaacccgacaggactat
aaagataccaggcgtttccccctggaagctccctcgtgcgctctcctgtt
ccgaccctgccgcttaccggatacctgtccgcctttctcccttcgggaag
cgtggcgctttctcatagctcacgctgtaggtatctcagttcggtgtagg
tcgttcgctccaagctgggctgtgtgcacgaaccccccgttcagcccgac
cgctgcgccttatccggtaactatcgtcttgagtccaacccggtaagaca
cgacttatcgccactggcagcagccactggtaacaggattagcagagcga
ggtatgtaggcggtgctacagagttcttgaagtggtggcctaactacggc
tacactagaagaacagtatttggtatctgcgctctgctgaagccagttac
cttcggaaaaagagttggtagctcttgatccggcaaacaaaccaccgctg
gtagcggtggtttttttgtttgcaagcagcagattacgcgcagaaaaaa
ggatctcaagaagatcctttgatcttttctacggggtctgacgctcagtg
gaacgaaaactcacgttaagggattttggtcatga

Sequence Listing Free Text

Sequence of control plasmid (SEQ ID NO: 2):
CATAGCTTCAAAATGTTTCTACTCCTTTTTTACTCTTCCAGATTTTCTCG
GACTCCGCGCATCGCCGTAACCACCACACCCAAGCACAGCATACTA
AATTTCCCCTCTTTCTTCCTCTAGGGTGTCGTTAATTACCCGTACTAAAG
GTTTGGAAAAGAAAAAAGAGGCCGCCTCGTTTCTTTTTCTTCGTCGAAAA
AGGCAATAAAAATTTTTATCACGTTTCTTTTTCTTGAAAATTTTTTTTTT
GATTTTTTTCTCTTTCGATGACCTCCCATTGATATTTAAGTTAATAAACG
GTCTTCAATTTCTCAAGTTTCAGTTTCATTTTTCTTGTTCTATTACAACT
TTTTTTACTTCTTGCTCATTAGAAAGAAAGCATAGCAATCTAATCTAAGT
TTTCTAGATGGCTTCAAACTTTACTCAGTTCGTGCTCGTGGACAATGGTG
GGACAGGGGATGTGACAGTGGCTCCTTCTAATTTCGCTAATGGGGTGGCA
GAGTGGATCAGCTCCAACTCACGGAGCCAGGCCTACAAGGTGACATGCAG
CGTCAGGCAGTCTAGTGCCCAGAgAGAAAGTATACCATCAAGGTGGAGG
TCCCCAAAGTGGCTACCCAGACAGTGGGCGGAGTCGAACTGCCTGTCGCC
GCTTGGAGGTCCTACCTGAACATGGAGCTCACTATCCCAATTTTCGCTAC
CAATTCTGACTGTGAACTCATCGTGAAGGCAATGCAGGGGCTCCTCAAAG
ACGGTAATCCTATCCCTTCCGCCATCGCCGCTAACTCAGGTATCTACagc
gctGGAGGAGGTGGAAGCGGAGGAGGAGGAAGCGGAGGAGGAGGTAGCgg
acctaagaaaagaggaaggtggcggccgctGGTTCCGGACGGGCTGACG
CATTGGACGATTTTGATCTGGATATGCTGGGAAGTGACGCCCTCGATGAT
TTTGACCTTGACATGCTTGGTTCGGATGCCCTTGATGACTTTGACCTCGA
CATGCTCGGCAGTGACGCCCTTGATGATTTCGACCTGGACATGCTGATTA
ACTCTAGATGAgcggatctcttatgtctttacgatttatagttttcatta
tcaagtatgcctatattagtatatagcatctttagatgacagtgttcgaa
gtttcacgaataaaagataatattctacttttttgctcccaccgcgtttgc
tagcacgagtgaacaccatccctcgcctgtgagttgtacccattcctcta
aactgtagacatggtagcttcagcagtgttcgttatgtacggcatcctcc
aacaaacagtcggttatagtttgtcctgctcctctgaatcgagtccctcg
atatttctcatactagttctagagatcgagctcgtttttcgacactggatg
gcggcgttagtatcgaatcgacagcagtatagcgaccagcattcacatac
gattgacgcatgatattacttctgcgcacttaacttcgcatctgggcag
atgatgtcgaggcgaaaaaaatataaatcacgctaacatttgattaaaa
tagaacaactacaatataaaaaaactatacaaatgacaagttcttgaaaa
caagaatcttttttattgtcagtactgattagaaaaactcatcgagcatca
aatgaaactgcaatttattcatatcaggattatcaataccatatttttga
aaaagccgtttctgtaatgaaggagaaaactcaccgaggcagttccatag
gatggcaagatcctggtatcggtctgcgattccgactcgtccaacatcaa
tacaacctattaatttccccctcgtcaaaaataaggttatcaagtgagaaa
tcaccatgagtgacgactgaatccggtgagaatggcaaaagcttatgcat
ttctttccagacttgttcaacaggccagccattacgctcgtcatcaaaat
cactcgcatcaaccaaaccgttattcattcgtgattgcgcctgagcgaga
cgaaatacgcgatcgctgttaaaaggacaattacaaacaggaatcgaatg
caaccggcgcaggaacactgccagcgcatcaacaatatttcacctgaat
caggatattcttctaatacctggaatgctgttttgccggggatcgcagtg
gtgagtaaccatgcatcatcaggagtacggataaaatgcttgatggtcgg
aagaggcataaattccgtcagccagtttagtctgaccatctcatctgtaa
catcattggcaacgctaccttttgccatgtttcagaaacaactctggcgca
tcgggcttcccatacaatcgatagattgtcgcacctgattgcccgacatt
atcgcgagcccatttataccatataaatcagcatccatgttggaattta
atcgcggcctcgaaacgtgagtcttttccttacccatggttgcgaattga
tccggtaatttagtgtgtgtatttgtgtttgcgtgtctatagaagtatag
taatttatgctacaaaggacctaatgtataaggaaagaatatttagagaa
aagaagaaaacaagagttttatatacatacagagcacatgcatgccataT
TGTGAAGAGTCTTATACAGTTCCttcaaatatgtatccgctcatgagaa
ataaccctgataaatgcttcaataatattgaaaaaggaagagtatgagta
ttcaacatttccgtgtcgcccttattcccttttttgcggcattttgcctt
cctgtttttgctcacccagaaacgctggtgaaagtaaaagatgctgaaga
tcagttgggtgcacgagtgggttacatcgaactggatctcaacagcggta
agatccttgagagttttcgccccgaagaacgttttccaatgatgagcact
tttaaagttctgctatgtggcgcggtattatcccgtattgacgccgggca
agagcaactcggtcgccgcatacactattctcagaatgacttggttgagt
actcaccagtcacagaaaagcatcttacggatggcatgacagtaagaga
ttatgcagtgctgccataaccatgagtgataacactgcggccaacttact
tctgacaacgatcggaggaccgaaggagctaaccgcttttttgcacaaca
tgggggatcatgtaactcgccttgatcgttgggaaccggagctgaatgaa
gccataccaaacgacgagcgtgacaccacgatgcctgtagcaatggcaa
caacgttgcgcaaactattaactggcgaactacttactctagcttcccggc
aacaattaatagactggatggaggcggataaagttgcaggaccacttctg
cgctcggcccttccggctggctggtttattgctgataaatctggagccgg
tgagcgtggctctcgcggtatcattgcagcactggggccagatggtaagc
cctcccgtatcgtagttatctacacgacggggagtcaggcaactatggat
gaacgaaatagacagatcgctgagataggtgcctcactgattaagcattg
gtaactgtcagaccaagtttactcatatatactttagattgatttaaaaac
ttcatttttaatttaaaaggatctaggtgaagatcctttttgataaatgg
gccgcgttgctggcttttttccataggctccgcccccctgacgagcatca
caaaaatcgacgctcaagtcagaggtggcgaaacccgacaggactataaa
gataccaggcgtttccccctggaagctccctcgtgcgctctcctgttccg Sequence Listing Free Text accctgccgcttaccggatacctgtccgcctttctcccttcgggaagcgt
ggcgctttctcatagctcacgctgtaggtatctcagttcggtgtaggtcg
ttcgctccaagctgggctgtgtgcacgaaccccccgttcagcccgaccgc
tgcgccttatccggtaactatcgtcttgagtccaacccggtaagacacga
cttatcgccactggcagcagccactggtaacaggattagcagagcgaggt
atgtaggcggtgctacagagttcttgaagtggtggcctaactacggctac Sequence Listing Free Text actagaagaacagtatttggtatctgcgctctgctgaagccagttacctt
cggaaaaagagttggtagctcttgatccggcaaacaaaccaccgctggta
gcggtggttttttttgtttgcaagcagcagattacgcgcagaaaaaagga
tctcaagaagatcctttgatcttttctacggggtctgacgctcagtggaa
cgaaaactcacgttaagggattttggtcatga

What is claimed is:

1. A cell comprising a programmable transcription activator system, the system comprising:
   a programmable transcription activator comprising:
      a domain that specifically binds to a promoter; and
      a transcriptional activator domain;
   a polynucleotide comprising a coding region whose expression is required for cell viability of the cell;
   a promoter operably linked to the polynucleotide, the promoter comprising a binding site for the programmable transcription activator; and
   a non-essential coding region operably linked to the promoter.

2. The cell of claim 1, wherein the transcription activator domain comprises VP64, VP16, VPR, p65, Rta, EDLL, Gal4, TAD, TV, or SunTag.

3. The cell of claim 1, wherein the domain that specifically binds to the promoter comprises dCas9, Cas9 combined with a gRNA, nuclease-inactive CPF1, or a transcription activator-like effector (TALE).

4. The cell of claim 1, wherein the non-essential coding region encodes a polypeptide involved in cell growth, cell reproduction, producing a secondary metabolite, or modulating an immune response.

5. A cell comprising a programmable transcription repressor system, the system comprising:

a programmable transcription repressor comprising:
  a domain that specifically binds to a promoter; and
  a transcriptional repressor domain;
a polynucleotide comprising a coding region whose expression is toxic to cell viability of the cell;
a promoter operably linked to the polynucleotide, the promoter comprising a binding site for the programmable transcription repressor; and
a non-essential coding region operably linked to the promoter.

6. The cell of claim 5, wherein the transcriptional repressor domain comprises a KRAB domain.

7. The cell of claim 5, wherein the domain that specifically binds to the promoter comprises dCas9, Cas9 combined with a gRNA, nuclease-inactive CPF1, or a transcription activator-like effector (TALE).

8. The cell of claim 5, wherein the toxic coding region encodes a polypeptide that interferes with cell growth, interferes with central metabolism, interferes with cell reproduction, or interferes with an immune response.

9. The cell of claim 1, wherein the cell is a single-celled organism.

10. The cell of claim 1, wherein the cell is a cell of a multicellular organism.

11. The cell of claim 5, wherein the cell is a single-celled organism.

12. The cell of claim 5, wherein the cell is a cell of a multicellular organism.

* * * * *

UNITED STATES PATENT AND TRADEMARK OFFICE
CERTIFICATE OF CORRECTION

| | |
|---|---|
| PATENT NO. | : 11,834,665 B2 |
| APPLICATION NO. | : 16/611008 |
| DATED | : December 5, 2023 |
| INVENTOR(S) | : Michael J. Smanski et al. |

It is certified that error appears in the above-identified patent and that said Letters Patent is hereby corrected as shown below:

In the Claims

In Column 18, Line 57 (Claim 2): 'Ga14' should read -- Gal4 --

Signed and Sealed this
Ninth Day of July, 2024

*Katherine Kelly Vidal*

Katherine Kelly Vidal
*Director of the United States Patent and Trademark Office*